United States Patent
Mallone et al.

(10) Patent No.: US 9,708,583 B2
(45) Date of Patent: Jul. 18, 2017

(54) METHODS FOR STIMULATING ANTIGEN-SPECIFIC T CELL RESPONSES

(71) Applicants: INSERM (INSTITUT NATIONAL DE LA SANTE ET DE LA RECHERCHE MEDICALE), Paris (FR); UNIVERSITE PARIS DESCARTES, Paris (FR)

(72) Inventors: Roberto Mallone, Paris (FR); Georgia Afonso, Paris (FR)

(73) Assignees: INSERM (Institut National de la Sante et de la Recherche Medicale), Paris (FR); Universite Paris Descartes, Paris (FR)

( * ) Notice: Subject to any disclaimer, the term of this patent is extended or adjusted under 35 U.S.C. 154(b) by 5 days.

(21) Appl. No.: 14/785,924

(22) PCT Filed: Apr. 22, 2014

(86) PCT No.: PCT/EP2014/058051
§ 371 (c)(1),
(2) Date: Oct. 21, 2015

(87) PCT Pub. No.: WO2014/173858
PCT Pub. Date: Oct. 30, 2014

(65) Prior Publication Data
US 2016/0068808 A1 Mar. 10, 2016

(30) Foreign Application Priority Data
Apr. 23, 2013 (EP) ..................................... 13305530

(51) Int. Cl.
| | |
|---|---|
| *A61K 38/20* | (2006.01) |
| *C07K 14/545* | (2006.01) |
| *C12N 5/0783* | (2010.01) |
| *G01N 33/50* | (2006.01) |
| *G01N 33/564* | (2006.01) |
| *G01N 33/569* | (2006.01) |
| *G01N 33/574* | (2006.01) |

(52) U.S. Cl.
CPC ........ *C12N 5/0636* (2013.01); *A61K 38/2006* (2013.01); *C07K 14/545* (2013.01); *G01N 33/505* (2013.01); *G01N 33/564* (2013.01); *G01N 33/569* (2013.01); *G01N 33/56972* (2013.01); *G01N 33/574* (2013.01); *C12N 2501/115* (2013.01); *C12N 2501/22* (2013.01); *C12N 2501/2301* (2013.01); *C12N 2501/2302* (2013.01); *C12N 2501/2304* (2013.01); *C12N 2501/2307* (2013.01); *C12N 2501/25* (2013.01); *C12N 2501/26* (2013.01); *C12N 2501/999* (2013.01); *G01N 2333/57* (2013.01); *G01N 2333/70514* (2013.01); *G01N 2333/70517* (2013.01); *G01N 2469/10* (2013.01); *G01N 2500/10* (2013.01)

(58) Field of Classification Search
CPC .... A61K 38/20; C07K 14/545; C12N 5/0636; G01N 2333/545
See application file for complete search history.

(56) References Cited

FOREIGN PATENT DOCUMENTS

WO 2010/119033 A1 10/2010

OTHER PUBLICATIONS

Plebanski, M., et al. Dependency on interleukin-1 of primary human in vitro T cell responses to soluble antigens. Eur. J. Immunol., 1992, vol. 22, p. 2353-2358.*
Ben-Sasson et al., "IL-1 acts directly on CD4 T cells to enhance their antigen-driven expansion and differentiation", Proceedings of the National Academy of Sciences, Apr. 28, 2009, pp. 7119-7124, vol. 106, No. 17.
Oystein et al., "Lipoteichoic acid derived from Enterococcus faecalis modulates the functional characteristics of both normal peripheral blood leukocytes and native human acute myelogenous leukemia blasts", European Journal of Haematology, Aug. 30, 2011, pp. 340-350, vol. 73, No. 5.
Afonso et al., "Critical parameters in blood processing for T-cell assays: Validation on ELISpot and tetramer platforms", Journal of Immunological Methods, Jul. 31, 2010, pp. 28-36, vol. 359, No. 1-2.
Martinuzzi et al., "Serum-free culture medium and IL-7 costimulation increase the sensitivity of ELISpot detection", Journal of Immunological Methods, Jan. 29, 2008, pp. 61-70, vol. 333, No. 1-2.
Numerof et al., "Pro-interleukin-1beta production by a subpopulation of human T cells, but not NK cells, in response to interleukin-2", Cellular Immunology, Oct. 1, 1990, pp. 118-128, vol. 130, No. 1.

* cited by examiner

*Primary Examiner* — Robert Landsman
*Assistant Examiner* — Bruce D Hissong
(74) *Attorney, Agent, or Firm* — Whitham, Curtis & Cook, P.C.

(57) ABSTRACT

The present invention relates to methods for stimulating antigen-specific T cell responses. In particular, the invention relates to a method for stimulating antigen (Ag)-specific T cell responses in a blood sample or PBMC sample isolated from a subject comprising the step consisting in culturing said blood or PBMC sample in a appropriate culture medium which comprises an amount of IL-1beta and an amount of a least one antigen.

13 Claims, 7 Drawing Sheets

METHODS FOR STIMULATING ANTIGEN-SPECIFIC T CELL RESPONSES

FIELD OF THE INVENTION

The present invention relates to methods for stimulating antigen-specific T cell responses.

BACKGROUND OF THE INVENTION

Study of antigen (Ag)-specific T cell responses poses formidable technical challenges [Kern, Trends Immunol. 26:477, 2005]. This is mainly due to the fact that Ag-specific fractions are commonly represented at very low frequencies in peripheral blood, a feature which makes their detection troublesome [Mallone, Clin. Immunol. 110:232, 2004]. This detection is even more problematic when CD4+ T cells are considered, as these fractions are frequently present at even lower frequencies than their CD8+ counterparts [Homann, Nat. Med. 7:913, 2001; Seder, Nat. Immunol. 4:835, 2003]. Several detection strategies are currently available which allow to detect such Ag-specific T cells (CD4+ and CD8+) using a variety of structural or functional readouts [Kern, Trends Immunol. 26:477, 2005]. However, one drawback shared by all techniques is that Ag-specific CD4+ T cells can rarely be detected directly ex-vivo. Most commonly, these cells need to be preliminarily expanded through 5-14 d in vitro culture steps to reach the detection threshold [Mallone, Clin. Immunol. 110:232, 2004]. Recently, it was discovered that it is possible to stimulate Ag-specific T cell responses by co-culturing them with differentiating dendritic cells directly from unfractionated whole blood or peripheral blood mononuclear cell (PBMC) samples, using appropriate cytokine cocktails and culture conditions (WO 2010/119033 and Martinuzzi, Blood 118:2128, 2011). The method (named acDC technology), which provided considerable advantages, consists in a) culturing a blood or PBMC sample in a medium which comprises GM-CSF and IL-4 in the presence of an antigen, and then b) maturing the DCs with a cocktail of molecules such as tumor necrosis factor (TNF)-alpha, prostaglandin (PG)E2 and interleukin (IL)-1beta.

SUMMARY OF THE INVENTION

The present invention relates to methods for stimulating antigen-specific T cell responses. In particular, the invention relates to a method for stimulating antigen (Ag)-specific T cell responses in a blood sample or PBMC sample isolated from a subject comprising the step consisting in culturing said blood or PBMC sample in an appropriate culture medium which comprises an amount of IL-1beta and an amount of a least one antigen.

DETAILED DESCRIPTION OF THE INVENTION

The inventors now identified that the differentiation step of the acDC technology is not mandatory and it is possible with a unique interleukin (i.e. IL-1beta) to stimulate Ag-specific T cell responses from a PBMC or blood sample.

Thus, the invention relates to a method for stimulating antigen (Ag)-specific T cell responses in a blood sample or PBMC sample isolated from a subject comprising the step consisting in culturing said blood or PBMC sample in an appropriate culture medium which comprises an amount of IL-1beta and an amount of a least one antigen.

The term "PBMC" or "peripheral blood mononuclear cells" or "unfractionated PBMC", as used herein, refers to whole PBMC, i.e. to a population of white blood cells having a round nucleus, which has not been enriched for a given sub-population. Cord blood mononuclear cells are further included in this definition. Typically, the PBMC sample according to the invention has not been subjected to a selection step to contain only adherent PBMC (which consist essentially of >90% monocytes) or non-adherent PBMC (which contain T cells, B cells, natural killer (NK) cells, NK T cells and DC precursors). A PBMC sample according to the invention therefore contains lymphocytes (B cells, T cells, NK cells, NKT cells), monocytes, and precursors thereof. Typically, these cells can be extracted from whole blood using Ficoll, a hydrophilic polysaccharide that separates layers of blood, with the PBMC forming a cell ring under a layer of plasma. Additionally, PBMC can be extracted from whole blood using a hypotonic lysis which will preferentially lyse red blood cells. Such procedures are known to the expert in the art.

The term "blood sample" or "unfractionated blood sample" as used herein refers to a crude blood specimen which has been isolated from a subject and collected in tubes or other containers containing an appropriate anti-coagulant (e.g., lithium heparin or sodium citrate). Cord blood is further included in this definition. The blood sample is unfractionated whole blood and contains plasma and blood cells (red blood cells, white blood cells). It may be a freshly isolated blood sample (<48 h) or a blood sample which has been obtained previously and kept frozen until use.

The term "subject" as used herein refers to a mammalian, such as a rodent (e.g. a mouse or a rat), a feline, a canine or a primate. In some embodiments, said subject is a human subject. The subject according to the invention can be a healthy subject or a subject suffering from a given disease.

Any culture medium suitable for growth, survival and differentiation of PBMCs may be used. Typically, it consists of a base medium containing nutrients (a source of carbon, aminoacids), a pH buffer and salts, which can be supplemented with serum of human or other origin and/or growth factors and/or antibiotics to which IL-1beta and the antigen are added. Typically, the base medium can be RPMI 1640, DMEM, IMDM, X-VIVO or AIM-V medium, all of which are commercially available standard media.

In the embodiment of the invention where a blood sample rather than a PBMC sample is cultured, use of such base media is dispensable, and IL-1beta and the antigen can be added directly into the blood, which serves as a culture medium.

An essential feature of the invention is that the culture medium does not contain any differentiating agent as described in WO 2010/119033, i.e. Granulocyte/Macrophage Colony-Stimulating Factor (GM-CSF) and/or IL-4 and/or FMS-like tyrosine kinase 3 (Flt-3) ligand. Likewise said agents are not added to the blood sample.

According to the invention, the amount of IL-1beta is added directly in the sample once it is prepared (e.g. Day 0 or Day 1, as described in the EXAMPLE).

The cell culture may be performed at 37° C. in a 5% CO2 atmosphere, using tissue culture incubators suitable to this end.

As used herein the term "IL-1beta" has its general meaning in the art and refers to interleukin-1 beta. Typically, IL-1β is used in an amount comprised between 0.1 and 1,000 ng/ml, preferably between 1 and 100 ng/ml, even more preferably at about 10 ng/ml. IL-1β can be obtained from a variety of sources. It may be purified or recombinant IL-1β.

IL-1β is commercially available from different companies, for example R&D Systems or PeproTech.

In some embodiments, IL-1beta may be added in combination with at least one agent selected from the group consisting of tumor necrosis factor alpha (TNF-α), prostaglandin E2 (PGE2), anti-CD40 monoclonal antibodies (mAbs), CD40 ligand (CD40L) recombinant chimeric proteins, interferon-alpha (IFN-α), interferon-gamma (IFN-γ), interleukin-7 (IL-7), lipopolysaccharides (LPS), CpG oligodeoxynucleotides, polyinosinic:polycytidylic acid (poly I:C), Pam3CysSerLys4 (Pam3CSK4), and imiquimod. Combination of such agents may be used. Said agent(s) are agents known to stimulate immune responses, and the skilled person will be able to select the appropriate concentrations.

In one embodiment, the Ag-specific T cell responses are CD4+ T cell responses.

In another embodiment, the Ag-specific T cell responses are CD8+ T cell responses.

The term "antigen" ("Ag") as used herein refers to protein, peptide, nucleic acid (e.g. DNA plasmid) or tissue or cell preparations capable of eliciting a T cell response. In some embodiments, said Ag is a protein which can be obtained by recombinant DNA technology or by purification from different tissue or cell sources. Such proteins are not limited to natural ones, but also include modified proteins or chimeric constructs, obtained for example by changing selected aminoacid sequences or by fusing portions of different proteins. In another embodiment of the invention, said Ag is a synthetic peptide, obtained by Fmoc biochemical procedures, large-scale multipin peptide synthesis, recombinant DNA technology or other suitable procedures. In another embodiment of the invention, said Ag is a protein or peptide coded by a DNA or other suitable nucleic acid sequence which has been introduced in cells by transfection, lentiviral or retroviral transduction, mini-gene transfer or other suitable procedures. In another embodiment of the invention, the Ag is a crude tissue or cell preparation (e.g., live cells or apoptotic cells/bodies) or a partially purified tissue or cell preparation obtained by different biochemical procedures (e.g., fixation, lysis, subcellular fractionation, density gradient separation) known to the expert in the art.

In some embodiments, said Ag is a protein which can be obtained by recombinant DNA technology or by purification from different tissue or cell sources. Typically, said protein has a length higher than 10 aminoacids, preferably higher than 15 aminoacids, even more preferably higher than 20 aminoacids with no theoretical upper limit. Such proteins are not limited to natural ones, but also include modified proteins or chimeric constructs, obtained for example by changing selected aminoacid sequences or by fusing portions of different proteins.

In another embodiment of the invention, said Ag is a synthetic peptide. Typically, said synthetic peptide is 3-40 aminoacid-long, preferably 5-30 aminoacid-long, even more preferably 8-20 aminoacid-long. Synthetic peptides can be obtained by Fmoc biochemical procedures, large-scale multipin peptide synthesis, recombinant DNA technology or other suitable procedures. Such peptides are not limited to natural ones, but also include modified peptides, post-translationally modified peptides or chimeric peptides, obtained for example by changing or modifying selected aminoacid sequences or by fusing portions of different proteins.

In another embodiment of the invention, said Ag is a protein or peptide coded by a DNA or other suitable nucleic acid sequence which has been introduced in cells by transfection, lentiviral or retroviral transduction, mini-gene transfer or other suitable procedures. The recipient cells may be either third party cells (e.g., cell lines obtained from the same PBMC/blood donor or from unrelated donors) or the same cells present in the unfractionated PBMC or blood sample used for stimulating T cell responses.

In another embodiment of the invention, the Ag is a tissue or cell preparation (e.g., live cells or apoptotic cells/bodies) or a crude or partially purified tissue or cell preparation obtained by different biochemical procedures (e.g., fixation, lysis, subcellular fractionation, density gradient separation) known to the expert in the art.

The skilled person in the art will be able to select the appropriate Ag, depending on the desired T cell stimulation.

In some embodiments, the method of the invention further comprises a step consisting of detecting stimulated T cells.

Methods for the detection of stimulated T cells are known to the skilled person. The procedures described below provide a few examples of suitable methods. However, the person skilled in the art can easily construe that any method suitable for assessing the stimulation of T cells in response to an Ag can be used.

In some embodiments, said method may consist in an enzyme-linked immunospot (ELISpot) assay. Non-adherent cells from pre-culture wells are transferred to a plate which has been coated with the desired anti-cytokine capture antibodies (Abs; e.g., anti-IFN-γ, -IL-10, -IL-2, -IL-4). Revelation is carried out with biotinylated secondary Abs and standard colorimetric or fluorimetric detection methods such as streptavidin-alkaline phosphatase and NBT-BCIP and the spots counted. ELISpot readouts are then expressed as spot-forming cells (SFC)/$10^6$ PBMCs.

In some embodiments, said method may consist in a supernatant cytokine assay. Cytokines released in the culture supernatant are measured by different techniques, such as enzyme-linked immunosorbent assays (ELISA), BD cytometric bead array, Biorad or Millipore cytokine mutiplex assays and others.

In some embodiments, the method may use HLA Class I or Class II multimers. With this procedure, Ag-reactive T cells recognizing specific peptide epitopes are detected, using either commercially available reagents (e.g., ProImmune MHC Class I Pentamers, Class II Ultimers; or Immudex MHC Dextramers) or in-house generated ones, e.g., from the NIH Tetramer Facility at Emory University, USA; from Dr. S. Buus, University of Copenhagen, Denmark [Leisner et al., *PLoSOne* 3:e1678, 2008], from Dr. G. T. Nepom, Benaroya Research Institute, Seattle, USA [Novak et al., *J. Clin. Invest.* 104:R63, 1999].

In some embodiments, the method is based on the detection of the upregulation of activation markers (e.g., CD69, CD25, CD137). With this procedure, Ag-specific T cell responses are detected by their differential expression of activation markers exposed on the membrane following Ag-recognition.

In some embodiments, the method may consist in a cytokine capture assay. This system developed by Miltenyi Biotech is a valid alternative to the ELISpot to visualize Ag-specific T cells according to their cytokine response. In addition, it allows the direct sorting and cloning of the T cells of interest (see below). In some embodiments, the method may consist in a CD154 assay. This procedure has been described in detail [Chattopadhyay et al., *Nat. Med.* 11:1113, 2005; Frentsch et al., *Nat. Med.* 11: 1118, 2005]. It is limited to detection of Ag-specific CD4+ T cells.

In some embodiments, the method may consist in a CD107 assay. This procedure [Betts et al., *J. Immunol.*

*Methods* 281:65, 2003] allows the visualization of Ag-specific CD8+ T cells with cytotoxic potential.

In some embodiments, the method may consist in a CFSE dilution assay. This procedure detects Ag-specific T cells (CD4+ and CD8+) according to their proliferation following Ag recognition [Mannering et al., *J. Immunol. Methods* 283:173, 2003].

The method of the invention may find various applications.

For example the method of the invention for stimulating Ag-specific T cell responses can be useful both for diagnosing a disease and for monitoring the immunological effects of an immune therapy in several settings.

Typically, in those embodiments, at least one disease associated antigens is used in the method of the invention.

In some embodiments, said disease is selected from the group consisting of autoimmune diseases. This group comprises, but is not limited to, type 1 diabetes (T1D), granulomatosis with polyangiitis (previously Wegener's granulomatosis), Crohn's disease, celiac disease and multiple sclerosis. In another embodiment of the invention, said disease is selected from the group consisting of cancer disease. This group comprises, but is not limited to, melanoma, colon cancer, renal cancer and haematological malignancies such as leukemias, lymphomas and multiple myeloma.

In another embodiment, said disease is selected from the group consisting of infectious diseases. This group comprises, but is not limited to, diseases caused by infectious agents such as M. tuberculosis, HIV, hepatitis C virus, cytomegalovirus, Epstein-Barr virus, adenoviruses, influenza viruses.

In another embodiment, said disease is a graft-vs-host disease complicating bone marrow transplantation and similar procedures.

For diagnostic applications, the method of the invention can be used to detect one or more Ag-specific T cell responses which are correlated with the disease, preferably an autoimmune disease. For example, the method can be used to detect preproinsulin- or glutamic acid decarboxylase (GAD)-specific T cell responses which are correlated with type 1 diabetes.

The expression "monitoring immune therapy" as used herein refers to measurement of changes in T cell responses induced in a given subject following in vivo administration of immune modulating agents. For monitoring applications, different types of situations are found, according to the type of disease. In autoimmune diseases, immune modulatory therapies can be used to blunt pathological immune responses. One strategy to accomplish this result relies on non-Ag-specific interventions based on a number of immune modulatory agents. For example, agents such as cyclosporin A (Stiller et al., Science 223:1362, 1984; Feutren et al., Lancet 19:119, 1986; Bougneres et al., Diabetes 39:1264, 1990), Daclizumab, mycophenolate mofetil, rapamycin, interleukin-2, anti-CD3 monoclonal antibodies (Herold et al., N. Engl. J. Med. 346:1692, 2002; Keymeulen et al., N. Engl. J. Med. 352:2598, 2005), anti-CD20 monoclonal antibodies such as Rituximab (Pescovitz et al., N. Engl. J. Med. 361:2143, 2009), autologous non-myeloablative hematopoietic stem cell transplantation (Voltarelli et al., JAMA 297:1568, 2007), autologous cord blood cell infusion (Haller et al., Diabetes Care 32:2041, 2009), vitamin D, T regulatory cell adaptive therapies have been, are being or are likely to be tested for T1D prevention and/or intervention. A second approach relies on Ag-specific strategies, i.e., administration of a disease-related Ag in a tolerogenic form. For example, agents such as (pro)insulin (DPT-1, N. Engl. J. Med. 346:1685, 2002; Skyler et al., Diabetes Care 28:1068, 2005; Nanto-Salonen et al., Lancet 372:1746, 2008; Fourlanos et al., Diabetes 60:1237, 2011), (pro)insulin-derived peptides (Orban et al., J. Autoimmun. 34:408, 2010; Thrower et al., Clin. Exp. Immunol. 155:156, 2009), GAD (Ludvigsson et al., N. Engl. J. Med. 359:1909, 2008; Wherrett et al., Lancet 378:319, 2011; Axelsson et al., PLoS One 6:e29008, 2011; Ludvigsson et al., N. Engl. J. Med. 366:433, 2012), NBI-6024 (Alleva et al., Scand. J. Immunol. 63:59, 2006), DiaPep277 (Raz et al., DiabetesMetab. Res. Rev. 23:292, 2007) and combinations thereof, anti-CD3 in combination with β-cell Ags (Bresson et al., J. Clin. Invest. 116:1371, 2006), in vitro or in vivo DC Ag loading (Mukhopadhaya et al., Proc. Natl. Acad. Sci. USA 105:6374, 2008), epitope-HLA multimers (Casares et al., Nat. Immunol. 3:383, 2002; Masteller et al., J. Immunol. 171:5587, 2003; Mallone et al., Blood 106:2798, 2005), L. lactis transgenically modified to produce the Ag of interest (Takiishi et al., J. Clin. Invest. 122:1717, 2012) have been, are being or are likely to be tested for T1D prevention and/or intervention.

In cancer and infectious diseases, pathogenesis is not driven by pathological immune responses, but rather by tissue cells or infectious agents which escape control by the immune system. Immune responses against cancer or infected cells/infectious agents are therefore physiological adaptations trying to counter-act disease. These physiological mechanisms can be therapeutically boosted, using either non-Ag-specific strategies (for example, cytotoxic T lymphocyte-associated antigen 4 blockade, alone or in combination with various agents, in melanoma; Yuan et al., Proc. Natl. Acad. Sci. USA 105:20410, 2008; Maker et al., Ann. Surg. Oncol. 12:1005, 2005) or Ag-specific approaches, i.e., administration (so called vaccination) of disease-related Ag(s) in an immunogenic form. These latter approaches can be pursued by administering the Ag(s) alone or in combination with different adjuvant agents (for example, tumor-associated Ag administration in melanoma; Di Pucchio et al., Cancer Res. 66:4943, 2006; Peterson et al., J. Clin. Oncol. 21:2342, 2003; Bystryn et al., Clin. CancerRes. 7:1882, 2001); by administering DC pulsed with the Ag (for example, tumor-associated Ag-pulsed DC infusion in melanoma; Palucka et al., J. Immunother. 26:432, 2003; Banchereau et al., Cancer Res. 61:6451, 2001; Thurner et al., J. Exp. Med. 190:1669, 1999) or by adoptive transfer of disease-associated Ag-specific T cells (for example, tumor-associated Ag-specific T cell infusion in melanoma; Vignard et al., J. Immunol. 175:4797, 2005).

Therefore it is of therapeutic interest to follow the immune changes induced by such intervention. Successful interventions should translate in a decrease (in the case of autoimmune diseases) or increase (in the case of cancer and infectious diseases) of the disease-related Ag-specific T cell responses. Such changes in disease-related Ag-specific T cell responses could be either quantitative (e.g., change in the frequency of Ag-specific T cells) or qualitative (e.g., change in the phenotype and/or function of such T cells). Availability of these immune surrogate markers of clinical efficacy can be of great utility for a variety of applications. For example: better selection of patients to treat and therapeutic agents to use based on patient's immune responses (for example, GAD administration in patients presenting GAD-specific T cell responses); optimization and/or tailoring of therapeutic doses or administration regimens (for example, increase in doses/frequency of administration if no immune change is registered), thus improving the risk-tobenefit ratio; prognostic stratification of treated patients according to their probability to respond to treatment; decision of whether to treat patients again based on maintenance or not of the induced immune changes.

The method for stimulating Ag-specific T cell responses of the invention can therefore be very useful to monitor induction of these immune changes.

The expression "disease-associated antigens (Ags)", as used herein, refers to proteins or peptides which constitute the molecular targets of an immune response. Said molecular targets are expressed by the tissue(s) or cell(s) targeted by the immune response. Expression of disease-associated Ags can be limited to the target tissue or be extended to additional body compartments. Disease-associated Ags can be initially identified as being targets of autoantibody or T cell immune responses, or based on their selective expression by the target tissue. Some examples of disease-associated protein antigens are preproinsulin (PPI), glutamic acid decarboxylase (GAD), insulinoma-associated protein 2 (IA-2), islet-specific glucose-6-phosphatase catalytic-subunit-related protein (IGRP), zinc transporter 8 (ZnT8) and chromogranin A for T1D; myeloperoxydase and proteinase 3 for granulomatosis with polyangiitis; myelin oligodendrocyte glycoprotein (MOG) and myelin basic protein (MBP) in multiple sclerosis; gliadins in celiac disease; tyrosinase, melan-A, MART-1, gp100 and NY-ESO-1 in melanoma cancer; ESAT-6 for M. tuberculosis infection; gag for HIV infection; and hexon protein for adenovirus infection.

Examples of disease-associated peptide Ags are derived from the above said protein Ags following processing by Ag-presenting cells—including DC—and presentation in the context of different HLA Class I or Class II molecules. Therefore, said peptide Ags are different depending not only on their source Ag, but also on the HLA molecules by which they are presented. For example, a list of T1D-associated peptide Ags for both mouse and human can be found in DiLorenzo et al., Clin. Exp. Immunol. 148:1, 2007. Disease-associated peptide antigens also include post-translationally modified aminoacid sequences and sequences derived from alternative splicing isoforms.

The expression "disease-associated antigens" also refers to tissues or cells which constitute the targets of an immune response. Disease-associated tissues/cells can be identified as being targets of the disease based on pathophysiology and clinical presentation of said disease. Some examples of disease-associated tissues/cells are insulin-producing pancreatic beta-cells for T1D; oligodendrocytes in multiple sclerosis; intestinal epithelia in celiac disease; malignant melanocytes in melanoma cancer; M. tuberculosis for tuberculosis infection; and HIV for HIV infection.

The immune response mounted against disease-associated Ags can be a pathological one (i.e., in the case of autoimmune diseases) or a physiological, potentially beneficial one, aimed at limiting the consequences of another ongoing pathological process (i.e., in the case of cancer or infectious diseases). By virtue of the pathological or physiological immune responses underlying said diseases, detection of such responses can be used to diagnose these diseases, or to follow their natural or therapeutically modified evolution. By measuring disease-associated Ag-specific T cell responses, the method described herein can therefore be applied to both immune diagnosis and monitoring (e.g., immune staging, therapeutic follow-up) of said diseases.

The person skilled in the art will know how to select appropriate disease-associated Ags. Such selection is based on a wide array of strategies. Examples of such strategies for T1D-associated Ags can be found in Wenzlau et al. Proc. Natl. Acad. Sci. USA 2007; Peakman et al., J. Clin. Invest. 1999; Nepom et al., Proc. Natl. Acad. Sci. USA 2001; Arif et al., J. Clin. Invest. 2004; Toma et al., Proc. Natl. Acad. Sci. USA 2005; Blancou et al., J. Immunol. 2007; Skowera et al., J. Clin. Invest. 2009; Scotto et al., Diabetes 2012; Scotto, Afonso et al., Diabetologia 2012. Reviews of such strategies for T1D-associated peptide epitopes can be found in Di Lorenzo et al., Clin. Exp. Immunol. 148:1, 2007 and in Martinuzzi et al., Ann. N.Y. Acad. Sci. 1150:61, 2008.

Another application of the method of the invention concerns its use for the in vitro study of the immunogenicity (or tolerogenicity) of therapeutic proteins.

The term "therapeutic proteins" as used herein refers to protein or peptide compounds of any aminoacid length which are administered or are planned to be administered in vivo to human subjects to achieve a therapeutic effect. Examples of such therapeutic proteins are, but are not limited to, disease-associated Ags (as defined above), antibodies of different species (either in their native form or partially/fully humanized), cytokines, hormones or hormone analogues, coagulation factors, enzymes, bacterial or viral proteins. Such proteins are not limited to natural ones, but also include modified proteins or chimeric constructs, obtained for example by changing selected aminoacid sequences or by fusing portions of different proteins.

Without wishing to be bound by theory, there are two different therapeutic settings where evaluation of immunogenicity of therapeutic proteins is of relevance.

One first therapeutic setting concerns the use of disease-associated Ags (as defined above) for in vivo administration, with the aim of inducing a tolerogenic effect (e.g., in the case of autoimmune diseases) or an immunogenic effect (e.g., in the case of cancer or infectious diseases). It is important to first evaluate in vitro the potential to achieve said desired therapeutic effect.

In other therapeutic settings, the aim is not to induce immunogenic responses of any kind to the administered protein, but rather to avoid such responses so to allow said protein to achieve the therapeutic effect for which it is designed. Example of such settings include, without being limited to, cytokine-based immune therapies, hormone replacement therapies and replacement therapies for coagulation factors (e.g., Factor VIII in Haemophilia A) or enzymatic deficits (e.g., beta-glucuronidase in mucopolysaccharidosis VII). In all these situations, mounting of immunogenic responses against the administered protein is not desirable, as this would be counterproductive for achieving the desired therapeutic effect (e.g., side effects such as cytokine release syndromes; or neutralization/degradation of the therapeutic protein).

Another application of the method of the invention concerns its use for the in vitro study of vaccine adjuvants of potential relevance in human therapeutic settings.

The term "adjuvants" as used herein refer to pharmacological or immunological agents that enhance the immunogenicity of a vaccine by improving the quantity (i.e. frequency of responding immune cells) or quality of the immune response (e.g., polyfunctionality of the responding T cells, defined as the capability of said T cells to produce multiple cytokines and/or exert multiple effector functions; cytotoxicity against target cells presenting the cognate Ag(s); and/or functional avidity, defined as the strength of recognition of the cognate Ag(s) by T cells and the magnitude of effector functions resulting from such recognition). The described technology can be used to define in vitro the quantity and/or quality of T cell responses elicited upon Ag stimulation in the presence of said adjuvants.

Without wishing to be bound by theory, examples of vaccine adjuvants include toll-like receptor ligands, cytokines, bacterial compounds, toxins or toxoids (i.e. toxins devoid of toxic effects).

The described technologies can similarly be used to define in vitro the potential for an in vivo tolerogenic effect of agents that may blunt response to given Ag(s). Such agents can be of relevance for in vivo applications where Ag(s) are administered to blunt rather than to boost immune responses against said Ag(s), e.g. in autoimmune or graft-versus-host diseases.

Without wishing to be bound by theory, examples of tolerogenic agents include immunomodulatory cytokines such as IL-10 or transforming growth factor (TGF)-beta or chimeric proteins engaging negative co-stimulatory receptors such as Cytotoxic T-Lymphocyte Ag (CTLA)-4-Ig or IL-1 receptor antagonist.

Another application of the method of the invention is its use for Ag or epitope discovery (also known as "mapping"), i.e. for screening Ags and epitopes in order to select those eliciting an Ag-specific T cell response.

The term "epitope" as used herein refers to the portion of a protein Ag recognized by a T cell. Epitopes are peptides of different aminoacid length which can bind to major histocompatibility complex (MHC) Class I or Class II molecules. The peptide-MHC complex thus formed can be recognized by the T cell receptor (TCR) expressed on T cells, thus leading to T cell activation and mounting of epitope Ag-specific T cell responses.

As Ags and epitopes are the defined molecular targets of T cells, it is often relevant to precisely identify such targets to design appropriate proteins or peptides to be used for in vitro applications (e.g., detection of Ag-specific T cell responses for diagnostic, prognostic or therapeutic purposes) or for in vivo administration (e.g., Ag- or epitope-based tolerogenic therapies in autoimmune diseases; or Ag- or epitope-based vaccinations in cancer and infectious diseases). Furthermore, definition of common rules governing epitope binding to a given MHC molecule (e.g. HLA-A2, A*02:01; or HLA-DR4, DR*04:01) and/or triggering of TCR signalling and T cell activation is often pursued with the aim of developing computerized algorithms capable of predicting the behaviour of a given epitope. Developing of such algorithms frequently requires availability of large experimental data sets.

Said candidate Ag can also be tissue(s) or cell(s) targeted by an immune response or any type of cell coated, loaded or forced to express candidate Ags or epitopes by biochemical or molecular biology techniques known to the expert in the art.

Yet another application of the method of the invention concerns its use for producing polyclonal T cells and T cell lines or clones recognizing a given Ag or combination of Ags. Accordingly, the invention relates to a method for producing T cells displaying specific immunological properties from a subject comprising the steps consisting in performing the method of the invention and isolating at least one T cell displaying at least one specific immunological property. Said specific immunological properties include, but are not limited to, recognition by the isolated T cells of the Ag added during step a) and/or b). By way of example, said specific immunological properties may also include the production of IFN-γ or the ability to exert cytotoxic effects on cells presenting the recognized Ag. T cells producing IFN-γ or displaying cytotoxicity can be useful for example for treatment of cancer and infectious diseases. By way of example, another possible specific immunological property can be the production of IL-10. T cells producing IL-10 can be used as regulatory T cells for the treatment of autoimmune diseases.

The person skilled in the art is familiar with methods for expanding said Ag-specific T cells once isolated from a blood sample or a PBMC sample as needed. Examples of such methods can be found in Reijonen et al., *Diabetes* 51:1375, 2002; Mallone et al., *Blood* 106:2798, 2005; Mannering et al., *J. Immunol. Methods* 298:83, 2005; Yee et al., *J. Immunol.* 162:2227, 1999; Mandruzzato et al., *J. Immunol.* 169:4017, 2002; Oelke et al., *Nat. Med.* 9:619, 2003; Skowera et al., *J. Clin. Invest.* 118:3390, 2009.

The person skilled in the art is also familiar with methods suitable to isolate said Ag-specific T cells in a viable state based on different immunological properties. For example, selection of IFN-γ- or IL-10-producing T cells may be obtained by Miltenyi cytokine capture assays. As another example, selection of cytotoxic T cells may be obtained based on upregulation of CD107 [Betts et al., *J. Immunol. Methods* 281:65, 2003]. As yet another example, said T cells can be isolated by means of MHC Class I or Class II multimers [Mallone et al., *Diabetes* 53:971, 2004; Mallone et al., *Blood* 106:2798, 2005; Skowera et al., *J. Clin. Invest.* 118:3390, 2008; Ladell et al., *Immunity* 38:425, 2013].

The invention will be further illustrated by the following figures and examples. However, these examples and figures should not be interpreted in any way as limiting the scope of the present invention.

FIGURES

FIG. 1. IL-1β is the critical minimal ingredient for amplifying protein Ag-specific IFN-γ T-cell responses. (A) Unfractionated fresh PBMCs ($10^6$/well in 96-well flat-bottom plates) were cultured either in the presence (black bars) or absence (white bars) of TTX and of different cytokine combinations added at day 0 (GM-CSF/IL-4, IL-4, GM-CSF, no cytokines or Flt3L, as indicated), then at day 1, i.e. after the first 24 h (TNF-α, $PGE_2$, 10 ng/ml IL-1β and combinations thereof, as indicated; where "All" means TNF-α/$PGE_2$/IL-1β). All conditions also received IL-7 (0.5 ng/ml) at day 1. At the end of these 48 h, a 6-h IFN-γ ELISpot was performed as detailed in Methods. One representative experiment out of 3 performed on three different donors is shown, with results expressed as IFN-γSFC/$10^6$ PBMCs. Means±SE of triplicate well are displayed. The dotted line indicates TTX-specific IFN-γ responses obtained in the absence of cytokines (B) Summary of the results obtained on 3 different donors and expressed as TTX-specific IFN-γ fold responses compared to the "no cytokines" condition. Each bar represents mean±SE fold responses from the 3 experiments, where values from each individual experiment were basal-subtracted (i.e. net TTX responses after subtraction of responses in the absence of Ag). *$p<0.05$; **$p<0.01$. (C) PBMC stimulation was performed as before in the absence of cytokines, with or without the addition an anti-IL1β blocking antibody at day 0. Data representation is the same as for panel A and results refer to a representative experiment performed on three separate occasions.

FIG. 2. An IL-1β dose of 10 ng/ml added at either day 0 or day 1 is sufficient to amplify protein Ag-specific IFN-γ T-cell responses. (A) Unfractionated fresh PBMCs were stimulated as in FIG. 1A either in the presence (black bars) or absence (white bars) of TTX, with further addition of no cytokines, GM-CSF/IL-4 (day 0) followed by TNF-α/$PGE_2$/IL-1β/IL-7 (day 1) or IL-1β alone (10 ng/ml) added at either day 0 or day 1. At the end of these 48 h, a 6-h IFN-γ ELISpot was performed as detailed in Methods. One representative experiment out of 9 performed on 9 different donors is shown, with means±SE of triplicate wells displayed. (B) Summary of the results obtained on 9 different donors and expressed as TTX-specific IFN-γ fold responses compared to the "no cytokines" condition. Data representation is as for FIG. 1B. *$p<0.05$. (C) Summary of the results obtained on 5 different donors comparing different IL-1β concentrations added at either day 0 or day 1. Data representation is as for FIG. 2B. *$p=0.06$ compared to GM-CSF/IL-4+ All.

FIG. 3. An IL-1β dose of 10 ng/ml added at day 0 is sufficient to expand epitope Ag-specific CD8+ T cells. Unfractionated fresh PBMCs ($10^6$/well in 96-well flat-bottom plates) from a HLA-A2+ healthy donor (HLA-A*02:01) were stimulated either in the presence or absence of the HLA-A2-restricted Flu $MP_{58-66}$ peptide, with further addition of the indicated cytokine cocktails (where "All" means TNF-α/$PGE_2$/IL-1β/IL-7), as detailed in the Methods. These cultures were stained at day 10 with Flu $MP_{58-66}$ peptide-loaded HLA-A2 TMrs. Events gated on viable CD14/CD19/CD4-negative CD8+ cells are shown and percentages of TMr+ cells out of the total CD8+ population are given. Results refer to a representative experiment performed three times.

FIG. 4. IL-1β stimulation efficiently expands both memory and naïve epitope Ag specific CD8+ T Cells. (A) Unfractionated fresh PBMCs ($10^6$/well in 96-well flat-bottom plates) from a HLA-A2+ healthy donor (HLA-A*02:01) were stimulated in the presence of the HLA-A2-restricted Flu $MP_{58-66}$ or Melan-$A_{26-35}$ELA peptide, with further addition of the indicated cytokine cocktails (where "All" means TNF-α/$PGE_2$/IL-1β/IL-7), as detailed in the Methods. These cultures were stained at day 10 with Flu $MP_{58-66}$ or Melan-$A_{26-35}$ELA peptide-loaded HLA-A2 TMrs, as indicated. Each condition was stained with both Flu and Melan-A TMrs to control for the Ag specificity of the expansion. PBMCs stained with these TMrs directly ex vivo are depicted for comparison in the last row. Events gated on viable CD14/CD19/CD4-negative CD8+ cells are shown and percentages of TMr+ cells out of the total CD8+ population are given for each plot. The median fluorescence intensity of the TMr+ gate is further indicated for some plots. Results refer to a representative experiment performed three times. (B) TMr+ cells from IL-1β-stimulated cultures were single-cell sorted and expanded as detailed in Methods. Representative CD8+ clones obtained at the end of this expansion are shown. For Melan-A-specific expansion, 11.7% (14/120) of the seeded wells yielded visible growth, with 100% (14/14) of them testing Ag-specific by Melan-$A_{26-35}$ELA TMr staining Staining with a HLA-A2 TMr loaded with an irrelevant peptide is shown for further control.

FIG. 5. IL-1β does not induce significant DC differentiation. Unfractionated fresh PBMCs ($10^6$/well in 96-well flat-bottom plates) were stimulated for 48 h in the presence of the indicated cytokine cocktails: GM-CSF/IL-4, Flt3L or IL-1β (10 ng/mL) at day 0, followed by TNF-α/$PGE_2$/IL-1β/IL-7 ("All") at day 1 in the case of GM-CSF/IL-4 and Flt3L. At the end of this 48 h culture, adherent cells were recovered and stained for the indicated markers. Expression profiles for each cytokine cocktail are shown (continuous profiles) in comparison with those obtained in the absence of cytokines (same antibodies used; dotted profiles) and after staining with isotype control antibodies (dashed profiles). Histograms are gated on viable CD19/CD3-negative cells. Results refer to a representative experiment out of three independent ones.

EXAMPLE 1

Methods:
Antigens

Tetanus toxoid (TTX; Statens Serum Institut) was >99% pure and had an endotoxin concentration <0.035 EU/µg by Limulus lysate assay (Lonza). The peptides Flu matrix protein $(MP)_{58-66}$ (GILGFVFTL), melanoma antigen (Melan-A)$_{27-35}$ (AAGIGILTV), Melan-$A_{26-35}$ELA (ELAGIGILTV) were >85% pure (ChinaPeptides).

Accelerated Co-Cultured Dendritic Cell (acDC) Stimulation

Peripheral blood mononuclear cells (PBMCs) were isolated and used fresh as previously described[1,2]. On day 0, PBMCs were plated at $10^6$/100 µl/well in 96-well flat-bottomed plates with AIM-V medium (Invitrogen) and the following cytokines added or not in different combinations as detailed in the figure legends: granulocyte/macrophage colony-stimulating factor (GM-CSF; 1000U/ml; R&D Systems), interleukin (IL)-4 (500U/ml; R&D), Fms-like tyrosine kinase-3 ligand (Flt3L; 50 ng/mL; R&D). Protein antigens (4-40 ng/µL) were added at the same time at concentrations titrated according to the responses of each donor. In selected experiments, an anti-1β blocking antibody (clone AS10; R&D) was added at 10 µg/ml from the start of culture, as detailed in the figure legends. After 24 hours (i.e. on day 1), the following reagents were added in different combinations, as detailed in the figure legends: tumor necrosis factor (TNF)-α (1000 U/mL; R&D), IL-1β (10-50-100 ng/mL; R&D), IL-7 (0.5 ng/mL; R&D), IL-2 (0.5 U/ml; Proleukin), prostaglandin $E_2$ ($PGE_2$; 1 µM; Merck Calbiochem). When used, short peptide antigens (i.e. cut at optimal length for direct binding to the restricting HLA-A2 molecule) were added at day 1, at concentrations (0.06-10 µM) individually titrated for each donor. On day 2 (i.e. 48 hours after the start of culture), non-adherent cells were collected, washed, and analyzed. In some experiments, adherent cells were recovered for flow cytometry analysis of DC differentiation (see below).

Enzyme-Linked Immunospot (ELISpot)

Interferon (IFN)-γ ELIspot assays were performed as previously described[3]. Briefly, 96-well PVDF plates (Millipore) were coated overnight with an anti-IFN-γ antibody (U-Cytech). Plates were then washed and blocked with RPMI (Invitrogen) supplemented with 10% heat-inactivated human serum (PAA). At the end of the 48 hours of acDC stimulation, non-adherent cells were washed, resuspended in fresh AIM-V medium and plated in the coated Elispot plates at $10^5$ cells/well in triplicate wells. After a 6-hour incubation at 37° C. and 5% $CO_2$, plates were washed and the captured IFN-γ revealed with a biotin-conjugated anti-IFN-γ antibody (U-Cytech), alkaline phosphatase-conjugated extravidin and SigmaFast 5-bromo-4-chloro-3-indolyl phosphate/nitroblue tetrazolium (BCIP/NBT) tablets (both from Sigma). Spots were counted on a Bioreader 5000 Pro-SF reader (BioSys) and means of triplicate wells calculated. ELISpot readouts are expressed as spot-forming cells (SFCs)/$10^6$ PBMCs. The cut-off for a positive response was set at 3SD above the average basal activity (i.e. in the absence of antigen). These spontaneous background responses are either shown in each graph or otherwise subtracted from antigen (Ag)-specific responses.

CD8+ T-Cell Expansion and Human Leukocyte Ag (HLA) Class I Tetramer Assays

After 48 hours of acDC stimulation, 10% heat-inactivated fetal bovine serum (FBS, PAA) was added to each well. Each 2-3 days, half of the medium was replaced with fresh RPMI supplemented with 10% FBS. At day 10 after the start of acDC stimulation, non-adherent cells were recovered and stained with phycoerythrin (PE)-labeled HLA-A2 tetramers (TMrs) loaded with Flu $MP_{58-66}$, Melan-$A_{27-35}$ or Melan-$A_{26-35}$ELA. To this end, cells were incubated at ~0.5-1×10$^6$ cells/200 µL in a 50 nM dasatinib solution for 30 min at 37° C., washed and reacted with TMrs for 20 min at room temperature (RT). A pre-mix of antibodies to CD14/CD19 (PerCP-Cy5.5), CD4 (Alexa-700 or APC) and CD8 (APC or Alexa-700) was added for 15 min at 4° C., after which cells were incubated with LiveDead Aqua (Invitrogen/Molecular Probes) for 10 min at RT. After washing, cells were fixed with 3.2% paraformaldehyde solution during 20 min at RT and acquired on a BD LSRFortessa flow cytometer. For TMr staining analysis, cells were first gate on live cells, then on CD14/CD19-negative events and on CD4-negative/CD8+ ones.

T-Cell Cloning

For T-cell cloning experiments, cells were TMr-stained at day 10-12 as above and single CD8+ TMr+ cells sorted into each well of a 96-well U-bottom plate using a BD FACSAria II equipped with 488, 633 and 405 nm lasers. Each well contained a mix of 2×10$^5$ PBMC feeder cells irradiated at 5,000 rad from 3 different donors in 100 µL RPMI medium supplemented with 10% FBS, 100 U/mL penicillin, 100 µg/ml streptomycin, 2 µg/mL Fungizone, 5% Cellkine (Zeptometrix), 200 U/mL IL-2, 25 ng/mL IL-15 (R&D) and 1 µg/mL PHA-L. Plates were visually checked for growth after 1-2 weeks and transferred to 48-well plates for testing Ag-specificity by TMr staining and for further expansion.

DC Phenotyping and Depletion

After 48 hours of acDC stimulation, adherent cells were recovered and stained with anti-CD19, -CD80, -CD86, -HLA-DR, -CD14, -CD11c antibodies and with the LiveDead viability marker. For DC analyses, gate is on live CD19/CD3-negative cells.

Statistical Analyses

All analyses were performed using GraphPad Prism 5 and FlowJo softwares. P values were calculated by paired Student t test or by Wilcoxon signed rank test according to distribution.

Figure 1A:
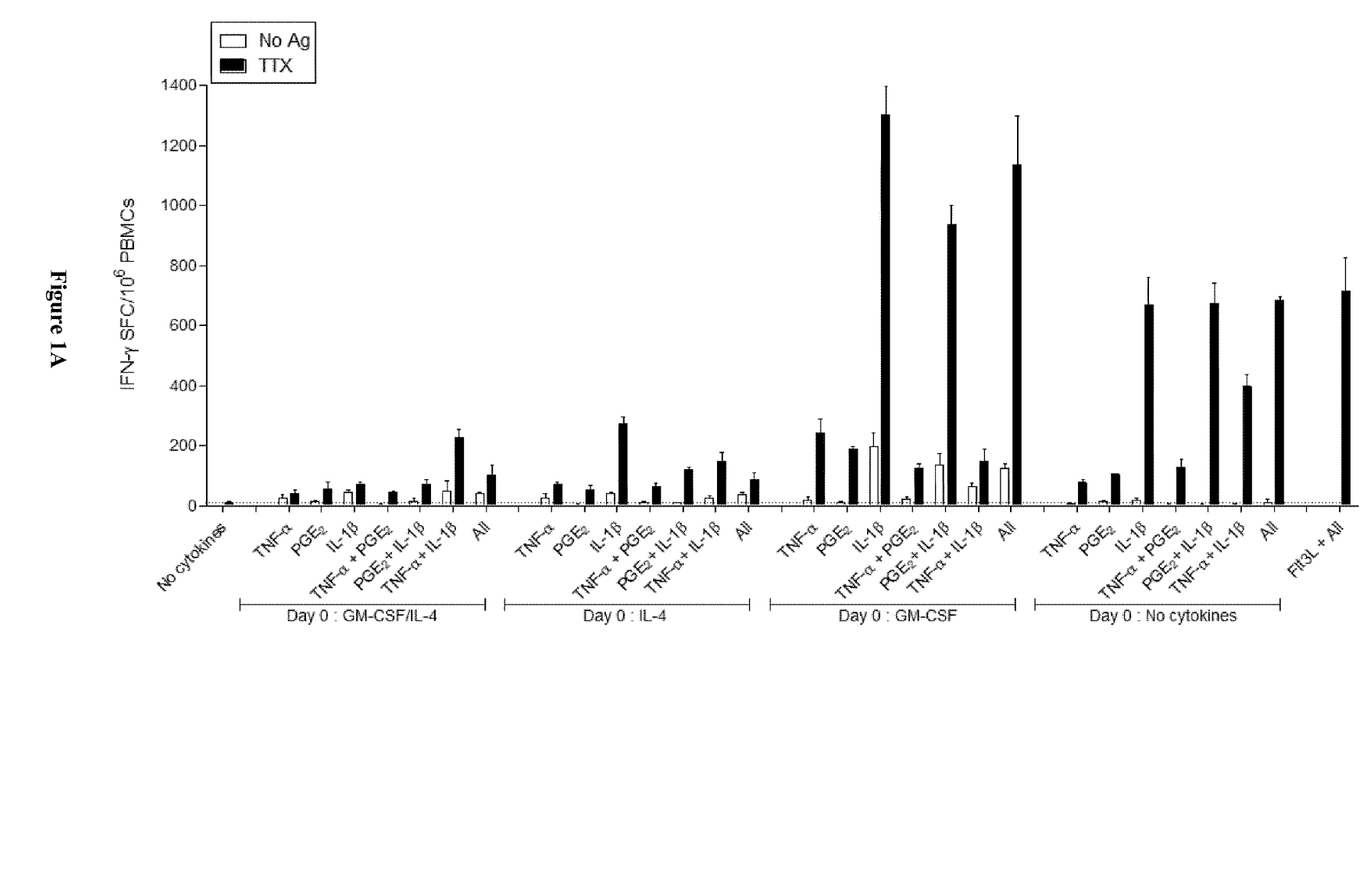
Figure 1B:
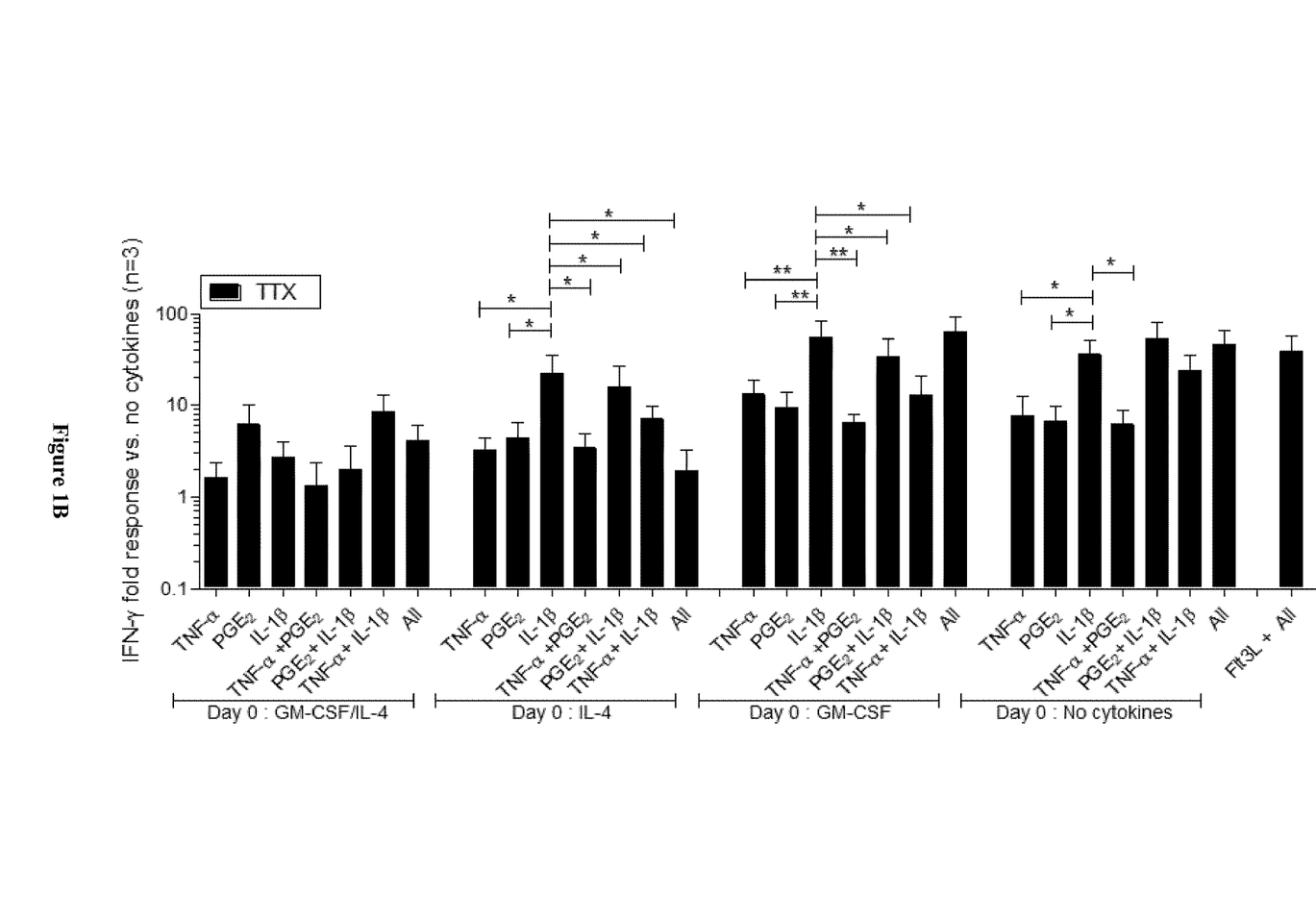
Figure 1C:
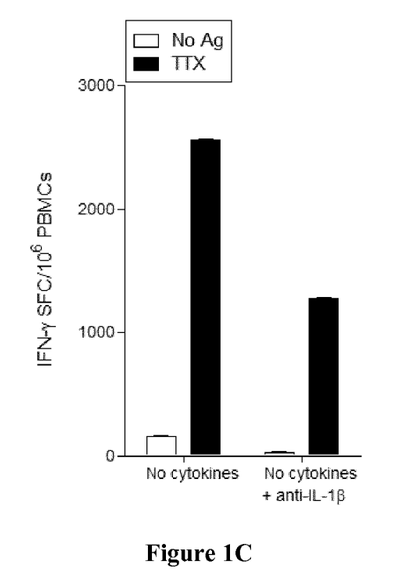
Figure 2A:
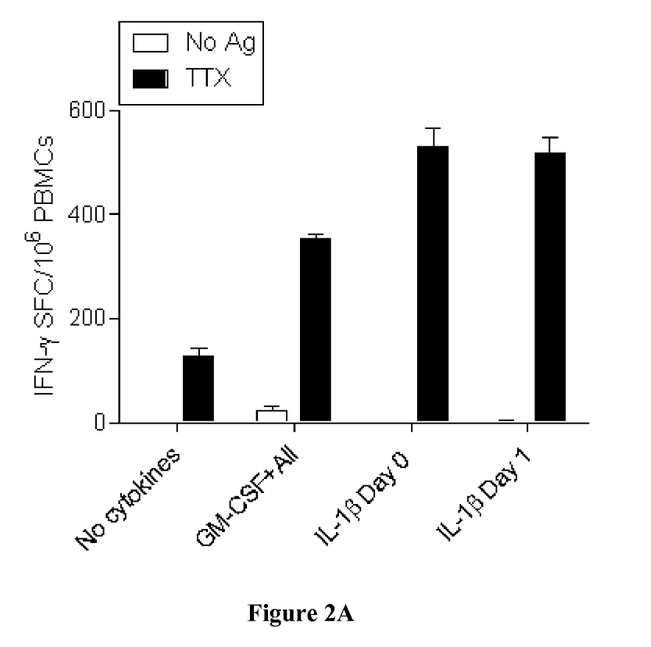
Figure 2B:
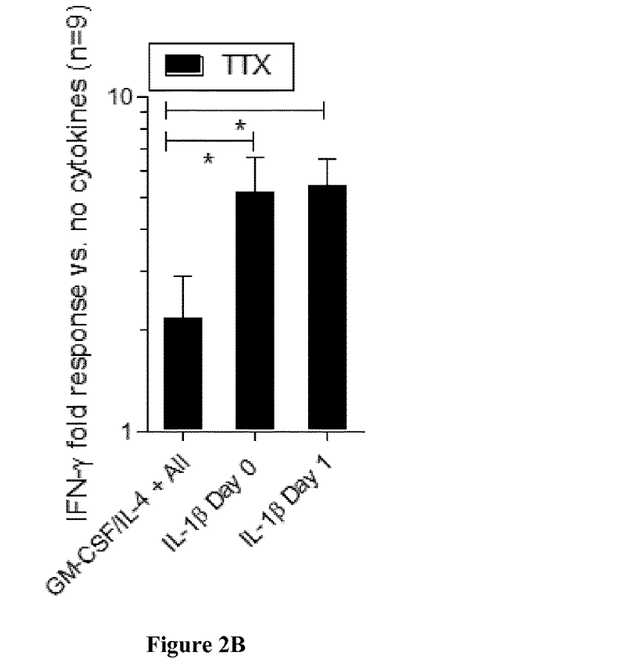
Figure 2C:
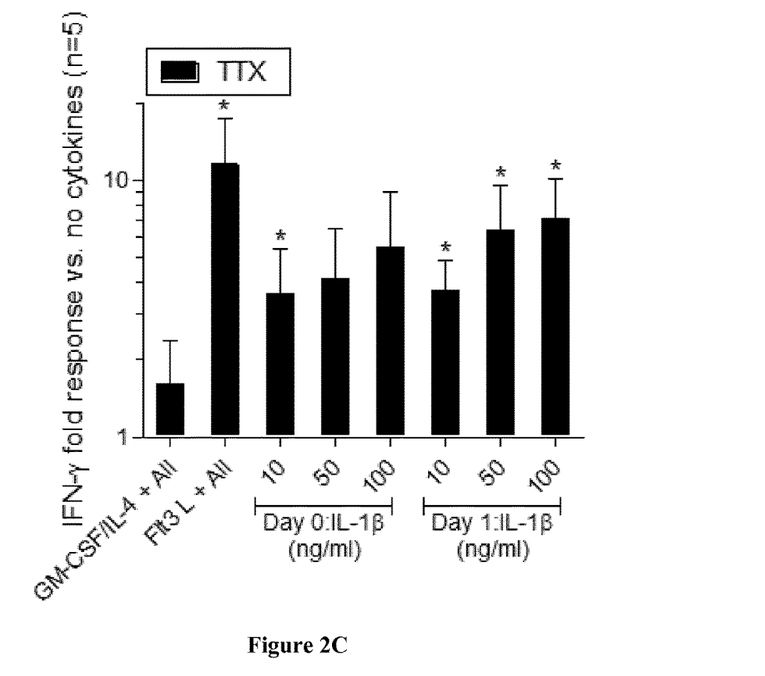
Figure 3:
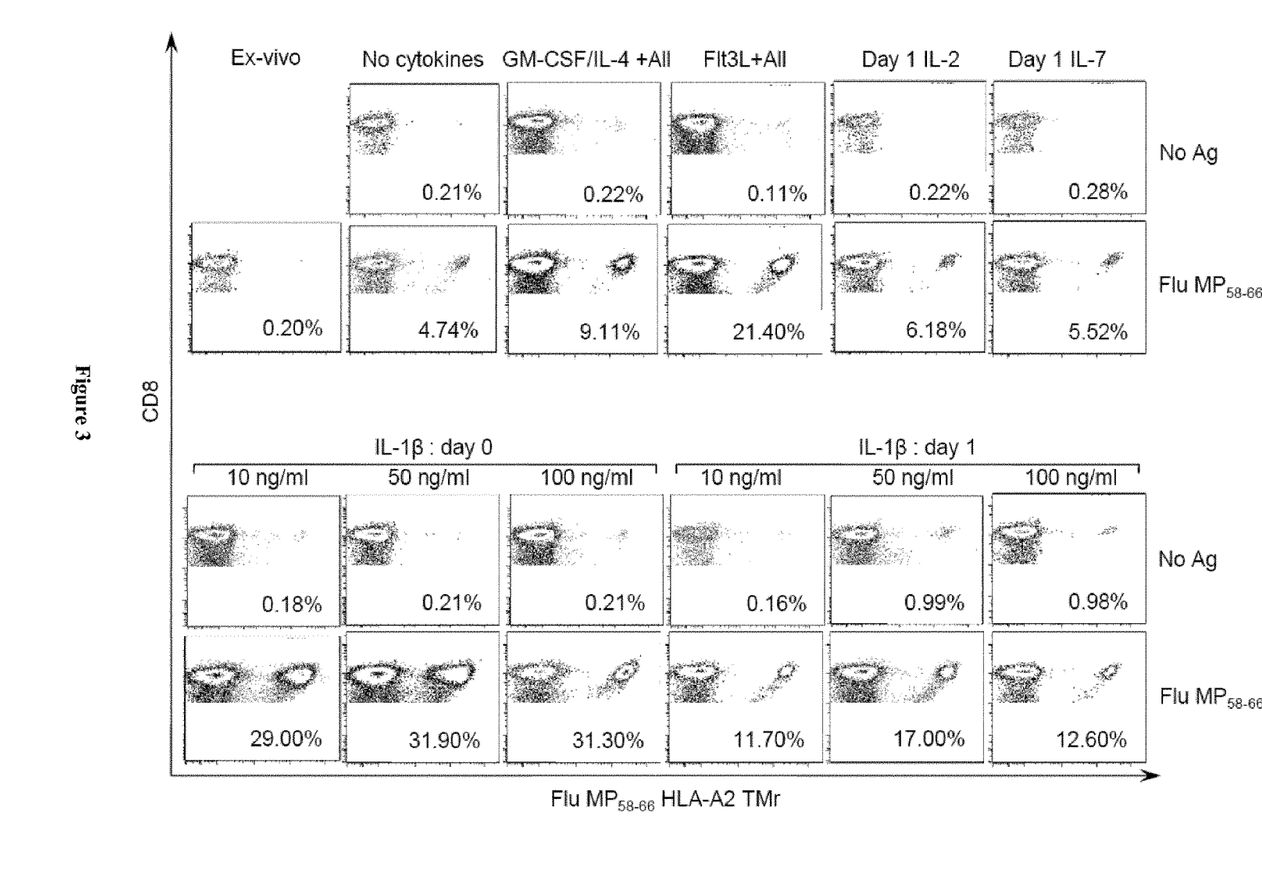
Figure 4A:
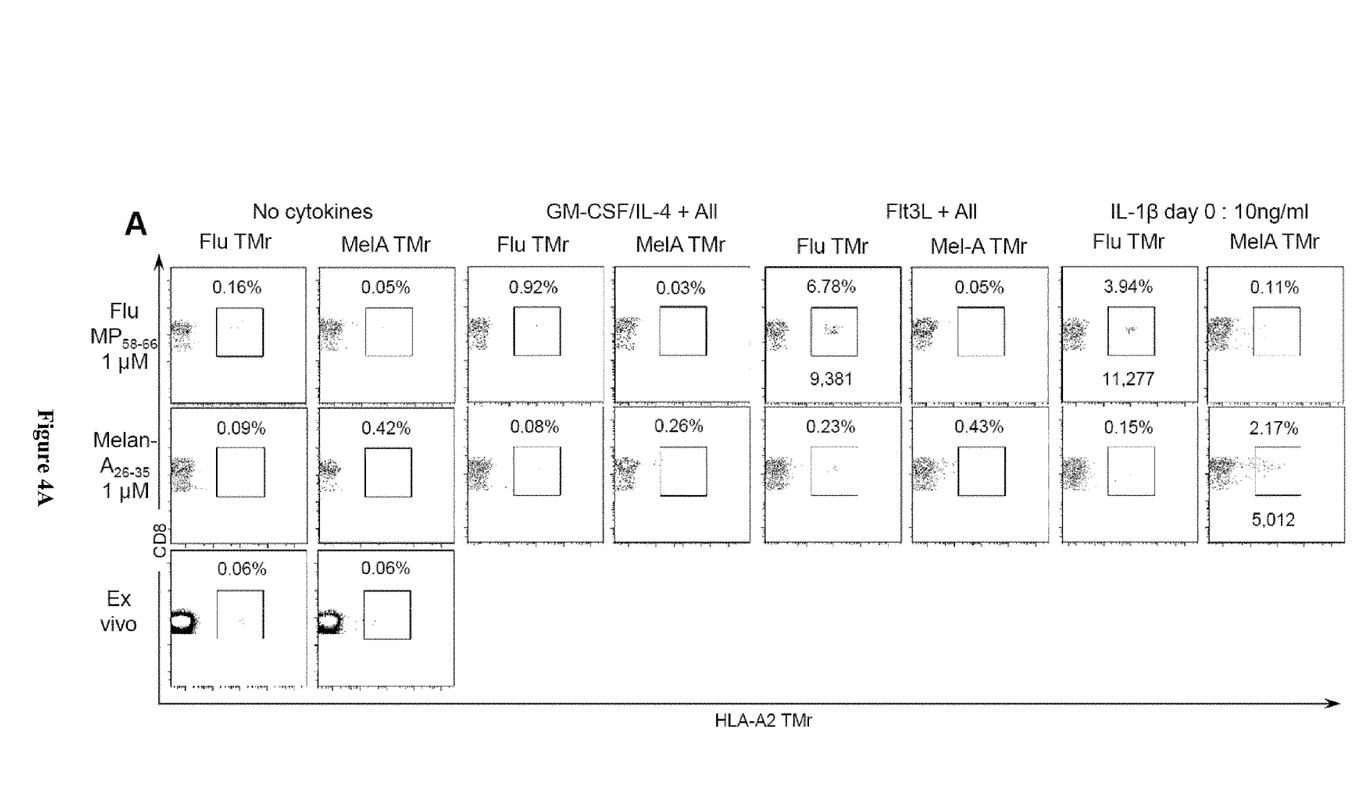
Figure 4B:
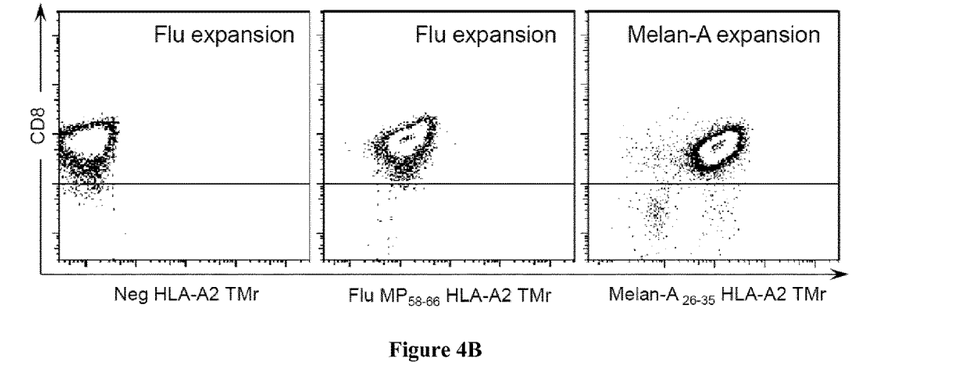
Figure 5:
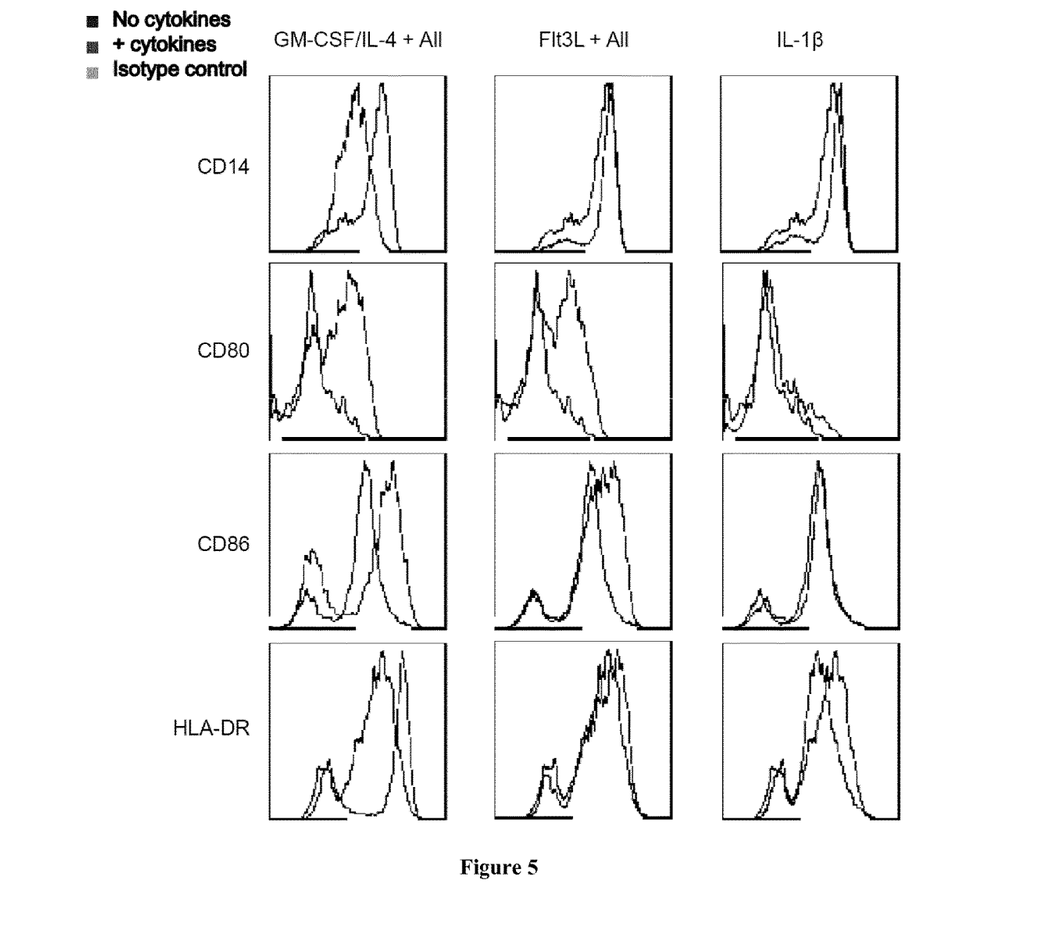

Results:

Altogether, the data provided show that IL-1beta is the minimal critical ingredient needed for efficient amplification of Ag-specific T cell responses using the previously described acDC cultures, in which DCs are differentiated in situ from PBMCs in two steps: a) GM-CSF/IL-4 or Flt3L added at Day 0; and b) TNF-alpha, PGE2, IL-1beta and IL-7 or other cytokine cocktails added at Day 1. Combinatorial analyses of cocktails in which different ingredients are omitted indicate that similar or better results are obtained when IL-1beta alone is used (FIG. 1). In other words, IL-1beta alone is sufficient to amplify Ag-specific T cell responses when compared to PBMC cultures carried out in the absence of cytokines (FIG. 1A-B). This IL-1beta-mediated amplification takes place also in unmanipulated conditions, because IL-1beta blocking in PBMCs cultured with Ag and in the absence of cytokines decreases Ag-specific T cell responses (FIG. 1C). The minimal effective dose is of 10 ng/ml and addition at either day 0 or day 1 is equivalent for amplifying protein Ag-specific IFN-γ T-cell responses (FIG. 2). However, IL-1beta addition at day 0 is more efficient for expanding epitope Ag-specific CD8+ T cells and is not equivalent to more conventional cytokine co-stimulation in the presence of IL-2 or IL-7 (FIG. 3). Expansion is obtained for both memory and naïve epitope Ag specific CD8+ T Cells (FIG. 4A) and leads to effective generation of T-cell clones (FIG. 4B). Finally, this IL-1beta-mediated amplification of Ag-specific T-cell responses does not induce any detectable DC differentiation compared to the previously described acDC protocols (FIG. 5). Hence, this method carries all the advantages described for the previous acDC protocols by making use of a single cytokine ingredient. Without wishing to be exhaustive, the main advantages are: rapidity and simplicity of use; detection sensitivity; minimal blood requirements; possibility to detect T cells recognizing multiple Ags or epitopes at once by working with cellular, protein or other crude Ag sources, making preliminary epitope and HLA identification dispensable; possibility to detect both CD4+ and CD8+ T cells; and possibility to expand Ag-specific T cells, both CD4+ and CD8+. While all these advantages are shared with the previous acDC methods, IL-1beta-based acDC cultures are characterized by improved ease of use and lower cost (by making use of a single cytokine) and by higher amplification of T-cell responses, resulting from higher Ag-specific and/or lower background T cell activation levels.

REFERENCES

Throughout this application, various references describe the state of the art to which this invention pertains. The disclosures of these references are hereby incorporated by reference into the present disclosure.

1. Afonso G, Scotto M, Renand A, et al. Critical parameters in blood processing for T-cell assays: validation on ELISpot and tetramer platforms. *J Immunol Methods.* 2010; 359(1-2):28-36.
2. Mallone R, Mannering S I, Brooks-Worrell B M, et al. Isolation and preservation of peripheral blood mononuclear cells for analysis of islet antigen-reactive T cell responses: position statement of the T-Cell Workshop Committee of the Immunology of Diabetes Society. *Clin Exp Immunol.* 2011; 163(1):33-49.
3. Fourlanos S, Perry C, Gellert S A, et al. Evidence that nasal insulin induces immune tolerance to insulin in adults with autoimmune diabetes. *Diabetes.* 2011; 60(4): 1237-45.
4. Martinuzzi E, Afonso G, Gagnerault M C, et al. acDCs enhance human antigen-specific T-cell responses. *Blood.* 2011; 118(8):2128-2137.
5. Axelsson S, Chéramy M, Hjorth M, et al. Long-lasting immune responses 4 years after GAD-alum treatment in children with type 1 diabetes. PLoS One. 2011; 6(12): e29008.
6. de Jongste A H, de Graaf M T, Martinuzzi E, et al. Three sensitive assays do not provide evidence for circulating HuD-specific T cells in the blood of patients with paraneoplastic neuro logical syndromes with anti-Hu antibodies. Neuro Oncol. 2012; 14(7):841-8.
7. Iglesias MC, Briceno O, Gostick E, et al. Immunodominance of HLA-B27-restricted HIV KK10-specific CD8(+) T-cells is not related to naïve precursor frequency. *Immunol Lett.* 2013 ; 149(1-2): 119-22.

The invention claimed is:

1. A method for stimulating antigen (Ag)-specific T cell responses in a blood sample or an unfractionated peripheral blood mononuclear cell (PBMC) sample isolated from a subject comprising the steps of culturing said blood or unfractionated PBMC sample in an appropriate culture medium which comprises an amount of interleukin-1 beta (IL-1β) and an amount of a least one antigen,
wherein the culture medium does not contain a differentiating agent selected from the group consisting of Granulocyte/Macrophage Colony-Stimulating Factor (GM-CSF), interleukin-4 (IL-4) and FMS-like tyrosine kinase 3 (Flt-3) ligand, and
  detecting amplification of a T cell response to said antigen in said blood sample or said unfractionated PBMC sample.

2. The method of claim 1 wherein said amount of IL-1β is from about 0.1 to about 1,000 ng/ml.

3. The method of claim 2, wherein said amount of IL-1β is from about 1 to about 100 ng/ml.

4. The method of claim 2, wherein said amount of IL-1β is about 10 ng/ml.

5. The method of claim 1 wherein the antigen is selected from the group consisting of proteins, peptides, nucleic acids, tissue preparations and cell preparations.

6. The method according to claim 1 wherein the antigen is a disease associated antigen.

7. The method according to claim 1 wherein the antigen is a therapeutic protein.

8. The method of claim 1, wherein said step of detecting is performed by detecting at least one of a CD4+ T cell response and a CD8+ T cell response.

9. An in vitro method for determining the immunogenic potential of a therapeutic protein in a subject in need thereof, comprising,
  stimulating antigen (Ag)-specific T cell responses in a blood sample or an unfractionated PBMC sample isolated from said subject by culturing said blood sample or said unfractionated PBMC sample in an appropriate culture medium which comprises an amount of IL-1β and an amount of said therapeutic protein, wherein the culture medium does not contain a differentiating agent selected from the group consisting of Granulocyte/Macrophage Colony-Stimulating Factor (GM-CSF), IL-4 and FMS-like tyrosine kinase 3 (Flt-3) ligand, and
  detecting amplification of a T cell response to said therapeutic protein in said blood sample or said unfractionated PBMC sample, wherein if an amplified T cell response is detected, then said therapeutic protein will be immunogenic in said subject, and if a T cell response is not detected, then said therapeutic protein will not be immunogenic in said subject.

10. An in vitro method for determining the immunogenic potential of a vaccine adjuvant in a subject, comprising,
  stimulating antigen (Ag)-specific T cell responses in a blood sample or an unfractionated PBMC sample isolated from said subject by culturing said blood sample or said unfractionated PBMC sample in an appropriate culture medium which comprises an amount of IL-1β and an amount of said vaccine adjuvant, wherein the culture medium does not contain a differentiating agent selected from the group consisting of Granulocyte/Macrophage Colony-Stimulating Factor (GM-CSF), IL-4 and FMS-like tyrosine kinase 3 (Flt-3) ligand, and
  detecting amplification of a T cell response to said vaccine adjuvant in said blood sample or said unfractionated PBMC sample, wherein if an amplified T cell response is detected, then said vaccine adjuvant will be immunogenic in said subject, and if a T cell response is not detected, then said vaccine adjuvant will not be immunogenic in said subject.

11. An in vitro method for evaluating potential of an agent to induce a tolerogenic effect in a subject in need thereof, comprising,
  stimulating antigen (Ag)-specific T cell responses in a blood sample or an unfractionated PBMC sample isolated from said subject by culturing said blood sample or said unfractionated PBMC sample in an appropriate culture medium which comprises an amount of IL-1β and an amount of said agent, wherein the culture medium does not contain a differentiating agent selected from the group consisting of Granulocyte/Macrophage Colony-Stimulating Factor (GM-CSF), IL-4 and FMS-like tyrosine kinase 3 (Flt-3) ligand, and
  detecting amplification of a T cell response to said agent in said blood sample or said unfractionated PBMC sample, wherein if an amplified T cell response is detected, then said agent will not induce a tolerogenic effect in said subject, and if a T cell response is not detected, then said agent will induce a tolerogenic effect in said subject.

12. An in vitro method for screening Ags and epitopes in order to select those eliciting an Ag-specific T cell response, comprising
  stimulating antigen (Ag)-specific T cell responses in a blood sample or an unfractionated PBMC sample isolated from a subject by culturing an amount of IL-1β and an amount of Ag or epitopes in culture medium that does not contain a differentiating agent selected from the group consisting of Granulocyte/Macrophage Colony-Stimulating Factor (GM-CSF), IL-4 and FMS-like tyrosine kinase 3 (Flt-3) ligand,
  detecting amplification of a T cell response to said Ag or epitope in said culture medium, and
  selecting Ags and epitopes which elicit said T cell response.

13. An in vitro method for producing polyclonal T cells and T cell lines or clones recognizing a Ag or combination of Ags, comprising
  stimulating antigen (Ag)-specific T cell responses in a blood sample or an unfractionated PBMC sample of isolated from said subject by culturing said sample in an appropriate culture medium which comprises an amount of IL-1β and an amount of said Ag or combination of Ags, wherein the culture medium does not contain a differentiating agent selected from the group consisting of Granulocyte/Macrophage Colony-Stimulating Factor (GM-CSF), IL-4 and FMS-like tyrosine kinase 3 (Flt-3) ligand, and
  detecting amplification of a T cell response to said Ag or combination of Ags in said T cells, and, if an amplified T cell response is detected in a T cell, then selecting said T cell for producing polyclonal T cells and T cell lines or clones which recognize said Ag or combination of Ags.

* * * * *